United States Patent [19]
Rossi

[11] Patent Number: 4,806,101
[45] Date of Patent: Feb. 21, 1989

[54] PORTABLE APPARATUS FOR REMOVING FOOD REMAINS FROM THE ORAL CAVITY

[76] Inventor: Gianfranco Rossi, 20 Via Enrico Panzacchi, I-00137 Roma RM, Italy

[21] Appl. No.: 174,455

[22] Filed: Mar. 23, 1988

[51] Int. Cl.$^4$ .............................................. A61C 17/04
[52] U.S. Cl. ........................................ 433/92; 433/91; 604/37; 604/316
[58] Field of Search ............... 433/91, 92, 95; 604/37, 604/75, 142, 316

[56] References Cited

U.S. PATENT DOCUMENTS

| | | | |
|---|---|---|---|
| 522,842 | 7/1894 | Lawshe | 433/92 |
| 530,556 | 12/1894 | Sherwin | 433/92 |
| 665,571 | 1/1901 | Metzler | 433/92 |
| 2,208,089 | 7/1940 | Grolman | 604/75 |
| 4,083,706 | 4/1978 | Wiley | 433/92 |

FOREIGN PATENT DOCUMENTS

| | | | |
|---|---|---|---|
| 372076 | 3/1923 | Fed. Rep. of Germany | 604/37 |
| 475462 | 11/1937 | United Kingdom | 604/316 |

*Primary Examiner*—John J. Wilson
*Attorney, Agent, or Firm*—Browdy and Neimark

[57] ABSTRACT

A portable apparatus for removing food remains from the oral cavity, particularly from the teeth. The apparatus includes a suction chamber, enclosing a removable filter, a suction member removably fixed to said suction chamber, a pipe in fluid communication with said suction chamber through a casing, and an outer cover of collapsible material removably fixed to said casing. Through depression upon said outer cover and, as a consequence, on said suction member, a depression is created inside the suction chamber, so that, through a pneumatic action, the food remains are moved from the oral cavity into the suction chamber where they are collected on said removable filter.

4 Claims, 3 Drawing Sheets

PORTABLE APPARATUS FOR REMOVING FOOD REMAINS FROM THE ORAL CAVITY

BACKGROUND OF THE INVENTION

The present invention relates to a portable apparatus for removing food remains from the oral cavity, particularly from the teeth. The removal of food remains from the teeth reduces caries, tendency to gengivitis and, moreover, the bad smell of the mouth, so improving oral hygene.

Apart from the usual toothbrush of prevailing domestic use, various systems for removing food remains are well known in the art. Relevant structural complexities, the use of electric power or batteries, and high costs are the main drawbacks of such systems and apparatuses belonging to the state of the art, for instance water pick, electric tooth brushes etc.

A main object of the present invention is to provide an apparatus for removing food remains due to mastication which have settled on the teeth, characterized by a surprisingly simple structure and operation, to allow the use at a very high degree of functionality and a remarkably low cost, in comparison with the apparatuses known in the art.

SUMMARY OF THE INVENTION

The subject of the present invention is a portable apparatus for removing food remains from the oral cavity which comprises:

(a) a suction chamber formed with a cap and base in threaded engagement, the cap having an upwardly extending tapered projection with a first through passage and the base having a downwardly extending projection with a second through passage and an annular outer groove, the first and second through passages being coaxial;

(b) a removable filter enclosed in the suction chamber;

(c) a suction member removably fixed to the outer groove of the downwardly extending projection;

(d) a substantially hemispherical casing having an inner cavity for receiving the suction chamber, a hole on the top coaxial to the first and second through passages, a lower rim formed with hooking means and a downwardly extending rib, integral with casing;

(e) a support fixed on top of the casing and having a channel aligned and in fluid communication with said first and second through passages;

(f) a pipe having an end sealingly engaged into the channel of said support and coaxial thereto and in fluid communication with the suction chamber and having the opposite end free;

(g) an outer cover of collapsible material removably fixed to the hooking means, and (h) a check valve connecting the suction member and said outer cover, so that upon pressing the outer cover of collapsible material and, as a consequence, the suction member, the check valve in this situation being closed, the food remains, as an effect of the depression, are moved from the oral cavity through the pipe and the first through passage of the cap and are held on the removable filter.

Other objects and features of the invention will be evident from the following detailed description of a preferred embodiment of the present invention.

DETAILED DESCRIPTION OF THE PREFERRED EMBODIMENT

Figure 2:
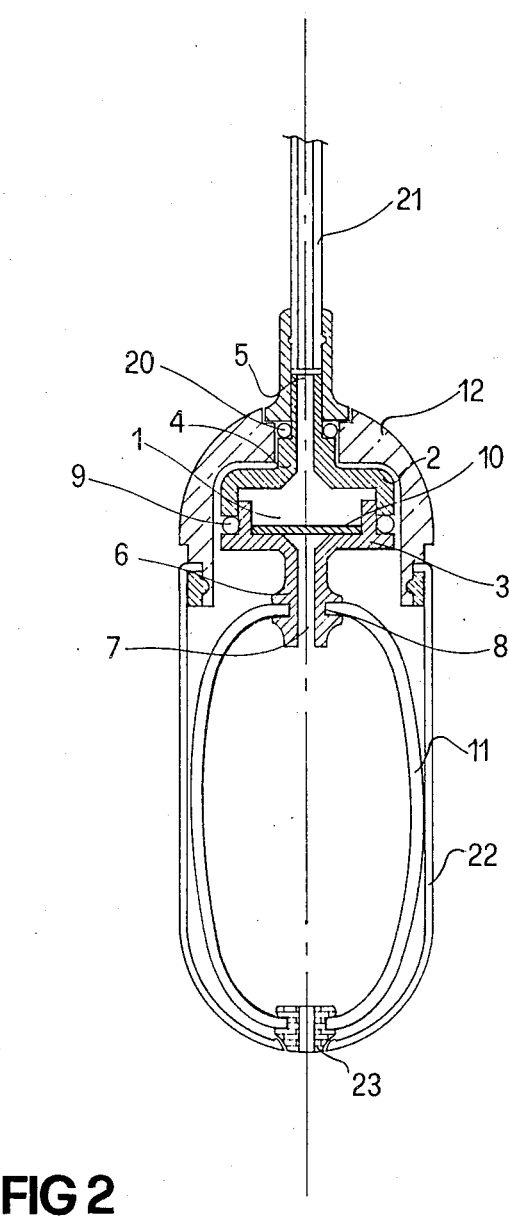
FIG. 2 shows a section, through line 2—2 in FIG. 1, of the apparatus according to the present invention.

With reference to FIG. 2, a suction chamber (1) is shown which is formed with a cap (2) and a base (3) threadedly engaged. The cap has an upwardly extending tapered projection (4) with a first through passage (5), while the base has a downwardly extending projection (6) with a second through passage (7). The downwardly extending projection is provided with an annular outer groove (8). The first and second through passages are aligned along the same axis. Between the cap and the base a first gasket (9) is placed. A filter (10) is removably placed on the base (3) inside the suction chamber (1). A suction member (11) is fixed to the annular outer groove (8) of the downwardly extending projection.

Figure 1:
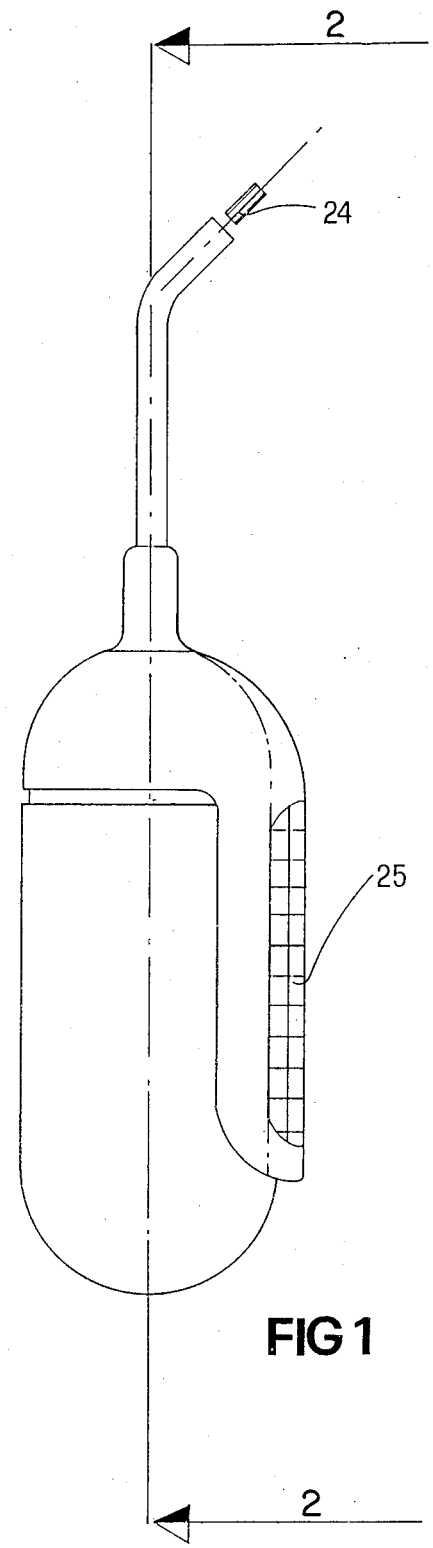
FIG. 1 shows, in side plan view, the apparatus according to the present invention.
Figure 3:
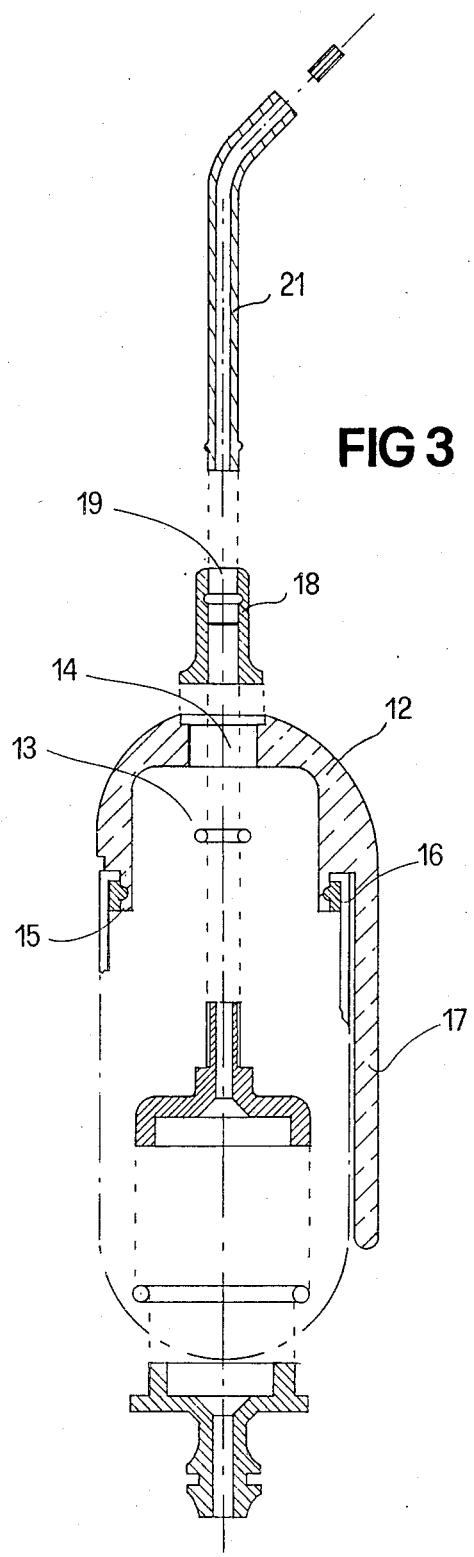
FIG. 3 is a cross-sectional exploded view of the apparatus according to the present invention.

Referring now to FIG. 3, a substantially hemispherical casing (12) is shown. The casing exhibits a hole (14) on the top which is coaxial to the first and second through passages and has an inner cavity (13) for receiving the suction chamber. Both the shape of the cap (2) and of the inner cavity (13) may vary according to the fabrication requirements. The casing (12) also shows a lower rim (15) which is formed with hooking means (16), which surround the whole casing except in one portion where a downwardly extending grip (17) integral with the casing is formed. The downwardly extending grip may be provided with a roughened area (25) for better gripping the apparatus according to the present invention. A support (18) having a channel (19) aligned and in fluid communication with the first and second through passages is fixed on the top of the casing (12). Referring again to FIG. 2, between the tapering of said upwardly extending projection of the cap and the support a second gasket (20) is placed. A pipe (21) is sealingly engaged with its lower end into the channel of the support and is coaxial thereto. The pipe is also in fluid communication with the suction chamber. The upper end of the pipe is free and its final part is also inclined with respect to its axis (see FIG. 1). An outer cover (22) of collapsible material is removably fixed to the hooking means. A check valve (23) connects the suction member (11) and the outer cover (22) and is placed at the bottom of the outer cover of collapsible material.

In a particularly preferred embodiment of the present invention (reference is made to FIG. 1) at the end of the pipe opposite to the end sealingly engaged into the support a crown (24) is placed, the crown having radial channels.

Upon pressing the outer cover of collapsible material and, as a consequence, the suction member, a depression is created inside the suction chamber because, in this situation, the check valve is closed. This depression inside the suction chamber is the driving force which makes it possible to move the food remains from the oral cavity, and particularly from the teeth, through the pipe and the first passage through the cap and to collect them on the removable filter. The construction characteristics of the apparatus according to the present invention allow a quick disassembly thereof and therefore the removal of food remains collected on the filter and the cleaning of the same apparatus can be performed easily. Through the operation of the crown having radial channels it is possible to avoid a sucker effect.

I claim:

1. Portable apparatus for removing food remains from the oral cavity which comprises:
   (a) a suction chamber formed with a cap and a base in threaded engagement, said cap having an upwardly extending tapered projection with a first through passage and said base having a downwardly extending projection with a second through passage and an annular outer groove, said first and second through passages being coaxial;
   (b) a removable filter enclosed inside said suction chamber;
   (c) a suction member removably fixed to said annular outer groove of said downwardly extending projection;
   (d) a substantially hemispherical casing having an inner cavity for receiving said suction chamber, a hole on the top coaxial to said first and second through passages, a lower rim formed with hooking means and a downwardly extending rib integral with said casing;
   (e) a support fixed on top of said casing and having a channel aligned and in fluid communication with said first and second through passages;
   (f) a pipe having an end sealingly engaged into the channel of said support and coaxial thereto and in fluid communication with said suction chamber and the opposite end free;
   (g) an outer cover of collapsible material removably fixed to said hooking means; and
   (h) a check valve connecting said suction member and said outer cover,
   so that upon pressing said outer cover of collapsible material and, as a consequence, said suction member, the check valve in this situation being closed, the food remains, as an effect of the depression, are moved from the oral cavity through said pipe and said first through passage of said cap and are collected on said filter.

2. Apparatus as claimed in claim 1, wherein the end of said pipe opposite to the end sealingly engaged into said support is inclined with respect to the axis of said pipe.

3. Apparatus as claimed in claim 1, wherein the end of said pipe opposite to the end sealingly engaged into said support is provided with a crown having radial channels.

4. Apparatus as claimed in claim 1, wherein between said cap and said base a first gasket is placed and between said upwardly extending projection of said cap and said support a second gasket is placed.

* * * * *